United States Patent
Chaney et al.

(10) Patent No.: US 9,220,511 B2
(45) Date of Patent: Dec. 29, 2015

(54) FEMORAL ORTHOPAEDIC SURGICAL INSTRUMENT INCLUDING A MEASUREMENT DEVICE AND METHOD OF USE OF SAME

(71) Applicant: DEPUY (IRELAND), Cork (IE)

(72) Inventors: Rebecca L. Chaney, Warsaw, IN (US); Craig S. Tsukayama, Fort Wayne, IN (US); Benjamin J. Sordelet, Fort Wayne, IN (US)

(73) Assignee: DePuy (Ireland) (IE)

( * ) Notice: Subject to any disclaimer, the term of this patent is extended or adjusted under 35 U.S.C. 154(b) by 354 days.

(21) Appl. No.: 13/780,836

(22) Filed: Feb. 28, 2013

(65) Prior Publication Data

US 2014/0243834 A1    Aug. 28, 2014

(51) Int. Cl.

| | | |
|---|---|---|
| A61B 17/58 | (2006.01) |
| A61B 17/60 | (2006.01) |
| A61F 2/00 | (2006.01) |
| A61B 17/15 | (2006.01) |
| A61F 2/46 | (2006.01) |
| A61F 2/38 | (2006.01) |
| A61F 2/30 | (2006.01) |
| A61B 17/72 | (2006.01) |

(52) U.S. Cl.
CPC .............. *A61B 17/155* (2013.01); *A61F 2/4657* (2013.01); *A61F 2/4684* (2013.01); *A61B 17/72* (2013.01); *A61F 2/3859* (2013.01); *A61F 2002/30594* (2013.01); *A61F 2002/30617* (2013.01); *A61F 2002/4658* (2013.01)

(58) Field of Classification Search
CPC combination set(s) only.
See application file for complete search history.

(56) References Cited

U.S. PATENT DOCUMENTS

| | | |
|---|---|---|
| 5,879,393 A | 3/1999 | Whiteside et al. |
| 6,013,081 A | 1/2000 | Burkinshaw |
| 6,056,756 A * | 5/2000 | Eng et al. .................... 606/87 |
| 6,080,196 A | 6/2000 | Bertin |
| 8,038,681 B2 | 10/2011 | Koenemann |
| 2004/0039450 A1 | 2/2004 | Griner et al. |
| 2007/0073305 A1 | 3/2007 | Lionberger et al. |
| 2009/0088762 A1 | 4/2009 | Koenemann |
| 2009/0125114 A1 | 5/2009 | May et al. |
| 2013/0325014 A1 | 12/2013 | Sordelet et al. |
| 2013/0325016 A1 | 12/2013 | Sordelet et al. |

(Continued)

FOREIGN PATENT DOCUMENTS

| | | |
|---|---|---|
| EP | 0914806 | 5/1999 |
| EP | 2042111 | 4/2009 |

OTHER PUBLICATIONS

European Search Report and Opinion for App. No. 1415416.6-1654, dated Mar. 13, 2014.

(Continued)

*Primary Examiner* — Sameh Boles
(74) *Attorney, Agent, or Firm* — Barnes & Thornburg LLP (57) ABSTRACT

An orthopaedic surgical instrument assembly is disclosed. The assembly includes an orthopaedic surgical instrument including a first surface, and a measurement gauge removably coupled to the orthopaedic surgical instrument. The gauge includes an arm having a tip positioned proximal to the orthopaedic surgical instrument, and a plurality of markings defined on the arm. Each marking indicates a predetermined distance from the first surface of the orthopaedic surgical instrument. The assembly may be used during an orthopaedic surgical procedure on a femur, which is also described herein.

7 Claims, 10 Drawing Sheets

(56) References Cited

U.S. PATENT DOCUMENTS

2013/0325018 A1 12/2013 Thomas et al.
2013/0325019 A1 12/2013 Thomas et al.
2013/0325021 A1 12/2013 Sordelet et al.
2013/0325136 A1 12/2013 Thomas et al.

OTHER PUBLICATIONS

GMK Revision, Surgical Technique, Ref. 99.27.12US rev. 1, Dec. 27, 1999, 74 pages.
Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
PFC Sigma RP-F, Specialist 2 Instruments, Surgical Technique, Performance in Flexion, 2007, 32 pages.
P.F.C. Sigma Rotating Platform Knee System with M.B.T Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.
Declaration of Gary M. Lindsay dated Dec. 23, 2014, 5 pages.
Redacted Memorandum with Appendix A, dated Jan. 26, 2010, outlining a surgical instrument evaluation that commenced in 2010, 37 pages.
"Reinstall Wave 1 Evaluation Surgical Technique," used during the surgical instrument evaluation that commenced in 2010, 36 pages.
Tray configuration cards showing the instruments used during the surgical instrument evaluation that commenced in 2010, 8 pages.

* cited by examiner

FEMORAL ORTHOPAEDIC SURGICAL INSTRUMENT INCLUDING A MEASUREMENT DEVICE AND METHOD OF USE OF SAME

Cross reference is made to copending U.S. patent application Ser. No. 13/485,470 entitled "METHOD OF SURGICALLY PREPARING A PATIENTS FEMUR," which issued as U.S. Pat. No. 9,050,107 on Jun. 9, 2015, which is assigned to the same assignee as the present application and is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, reamers, drill guides, prosthetic trials, and other surgical instruments to prepare the patient's bones to receive the knee prosthesis.

SUMMARY

According to one aspect of the disclosure, an orthopaedic surgical instrument assembly includes a cutting guide block and a measurement gauge removably coupled to the cutting guide block. The cutting guide block includes a base plate having a distal surface and a pair of curved arms extending posteriorly from the base plate. Each curved arm includes a posterior surface corresponding to a posterior condyle surface of a femoral prosthetic component. The gauge includes an arm having a tip positioned proximal to the base plate and a plurality of markings defined on the arm. Each marking indicates a predetermined distance between the marking and the distal surface of the base plate.

In some embodiments, the base plate of the cutting guide block may include a bore defined in a medial surface thereof, and the gauge may include a shaft attached to the arm. The shaft may be positioned in the bore of the base plate. In some embodiments, the shaft of the gauge may include a spring pin configured to couple the gauge to the cutting guide block.

Additionally, in some embodiments, the arm of the gauge may include a first segment having a first end secured to the shaft and a second end positioned distal to the base plate. The arm may also include a second segment having a first end attached to the second end of the first segment and a second end including the tip of the arm. The markings of the gauge may be defined on the second segment of the arm between the first end of the second segment and the second end of the second segment. The first segment and the second segment may define a J curve.

In some embodiments, the orthopaedic surgical instrument assembly may include a second measurement gauge removably coupled to the cutting guide block. The second measurement gauge may include an arm having a tip positioned proximal to the base plate and a plurality of second markings defined on the arm of the second measurement gauge. Each second marking may indicate a predetermined distance between the second marking and the distal surface of the base plate.

In some embodiments the orthopaedic surgical instrument assembly may include an intramedullary orthopaedic surgical instrument configured to be inserted into a medullary canal of a patient's femur, and an adaptor removably coupled to the cutting guide block and the intramedullary orthopaedic surgical instrument.

According to another aspect, an orthopaedic surgical instrument assembly includes an orthopaedic surgical instrument, an intramedullary orthopaedic surgical instrument removably coupled to the orthopaedic surgical instrument, and a measurement gauge removably coupled to the orthopaedic surgical instrument. The intramedullary orthopaedic surgical instrument has an end positioned proximal to the orthopaedic surgical instrument that is configured to be inserted into a medullary canal of a patient's femur. The gauge includes an arm having a tip positioned proximal to the orthopaedic surgical instrument and a plurality of markings defined on the arm. Each marking indicates a predetermined distance from the first surface of the orthopaedic surgical instrument.

In some embodiments, the orthopaedic surgical instrument may include a base plate including the first surface, and a pair of curved arms extending posteriorly from the base plate. In some embodiments, the intramedullary orthopaedic surgical instrument may have a longitudinal axis, and the arm of the gauge may include a segment extending parallel to the longitudinal axis.

According to another aspect, a method for performing an orthopaedic surgical procedure on a femur is disclosed. The femur includes a medial epicondyle, a lateral epicondyle, and an epicondylar axis extending through the medial epicondyle and the lateral epicondyle. The method includes assembling an orthopaedic surgical instrument assembly including a measurement gauge and an intramedullary orthopaedic surgical instrument, advancing the intramedullary orthopaedic surgical instrument into a distal opening of a medullary canal of the femur, and aligning a marking of the gauge with an end of the epicondylar axis such that a distal surface of the orthopaedic surgical instrument assembly is positioned a predetermined distance from the epicondylar axis.

In some embodiments, the marking may be defined on an anterior surface of the gauge. In some embodiments, the predetermined distance may be between approximately 2.5 and 4.0 centimeters.

Additionally, in some embodiments, the method may also include assessing a gap defined between the distal surface of the orthopaedic surgical instrument assembly and a tibial component attached to a corresponding tibia. In some embodiments, the method may include advancing the intramedullary orthopaedic surgical instrument deeper into the medullary canal of the femur, aligning a second marking of the gauge with the epicondylar axis to position the distal surface of the orthopaedic surgical instrument assembly a second predetermined distance from the epicondylar axis, and reassessing the gap defined between the distal surface of the orthopaedic surgical instrument assembly and the tibial component.

In some embodiments, the second predetermined distance may be between approximately 1.0 and 2.5 centimeters. In some embodiments, the method may also include attaching a second measurement gauge to the orthopaedic surgical instrument assembly, and aligning a marking of the second measurement gauge with the epicondylar axis.

In some embodiments, the measurement gauge may be a first measurement gauge, and the marking of the first measurement gauge may cooperate with the marking of the second measurement gauge to define an imaginary line indicating the epicondylar axis. The marking of the first measurement gauge may be aligned with the medial epicondyle and the marking of the second measurement gauge is aligned with the lateral epicondyle.

In some embodiments, the gauge may include a segment having a proximal end and a distal end, and a plurality of markings defined on the segment between the proximal end and the distal end. Each marking may indicate a different predetermined distance from the distal surface of the orthopaedic surgical instrument assembly. In some embodiments, aligning the marking of the gauge with the epicondylar axis may include selecting a first marking of the plurality of markings, and aligning the first marking with the epicondylar axis.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 1:
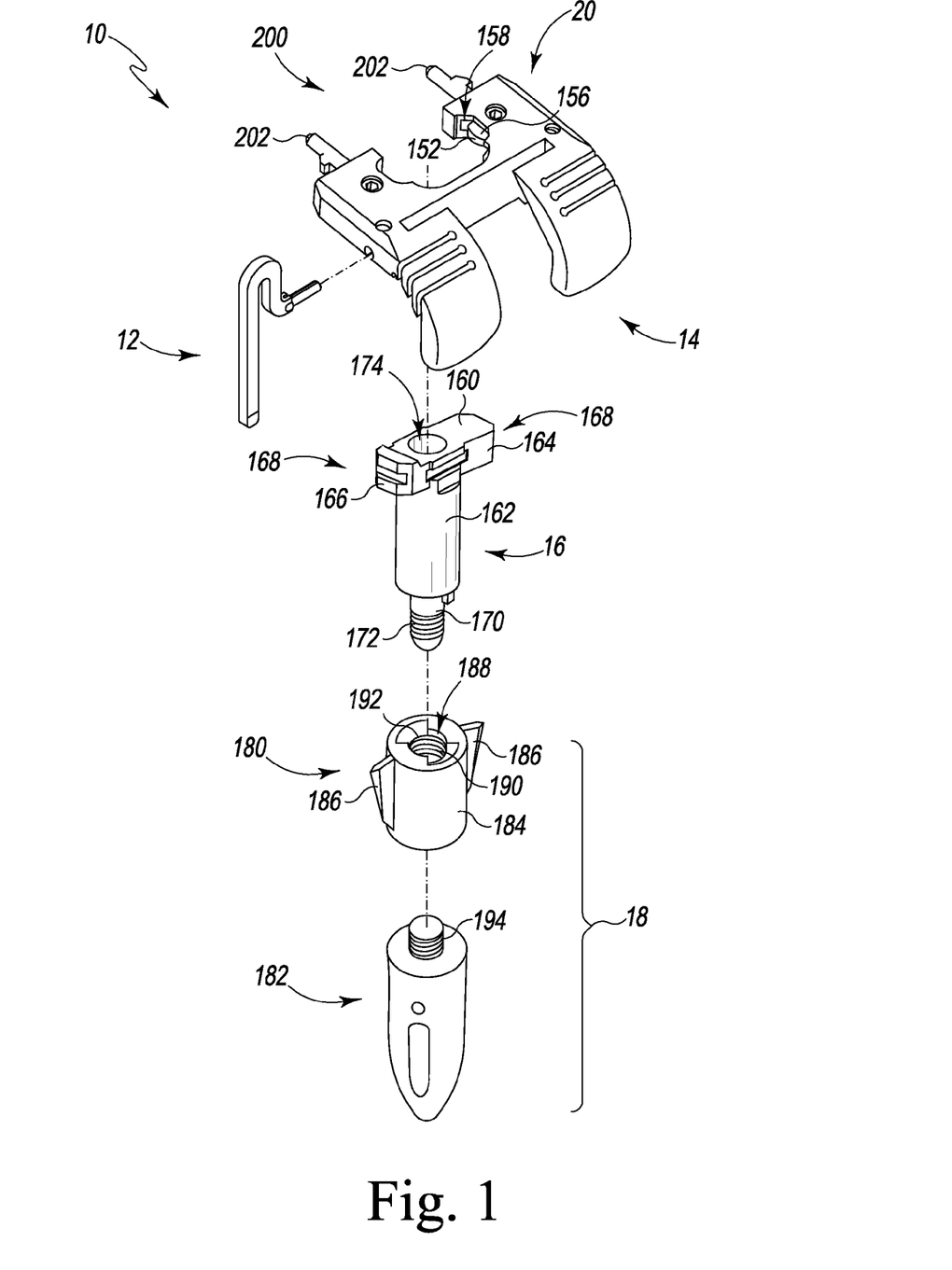
FIG. 1 is an exploded view of an exemplary embodiment of an orthopaedic surgical instrument assembly.

Referring now to FIG. 1, an orthopaedic surgical instrument assembly 10 (hereinafter instrument assembly 10) is shown. What is meant herein by the term "orthopaedic surgical instrument" or "orthopaedic surgical instrument assembly" is a surgical tool for use by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient. The instrument assembly 10 includes a measurement gauge 12 configured to be secured to a base cutting block 14. It should be appreciated that in other embodiments the instrument assembly 10 may include only a single measurement gauge 12, as described in greater detail below.

The instrument assembly 10 also includes an intramedullary adaptor 16 that is configured to be coupled to the base cutting block 14 and an intramedullary surgical instrument 18 that is configured to be secured to the intramedullary adaptor 16. What is meant herein by the term "intramedullary adaptor" is a surgical tool configured to be secured to an intramedullary orthopaedic surgical instrument and including an end sized and shaped to be positioned in a medullary canal of a patient's femur during the orthopaedic surgical procedure. What is meant herein by the term "intramedullary orthopaedic surgical instrument" is a surgical tool configured to be positioned in the medullary canal of the patient's femur during the orthopaedic surgical procedure. Examples of intramedullary orthopaedic surgical instruments include femoral stem trials, femoral broaches, and the like. The instrument assembly 10 also includes a locking mechanism 20 that secures the intramedullary adaptor 16 to the base cutting block 14, as described in greater detail below.

Figure 2:
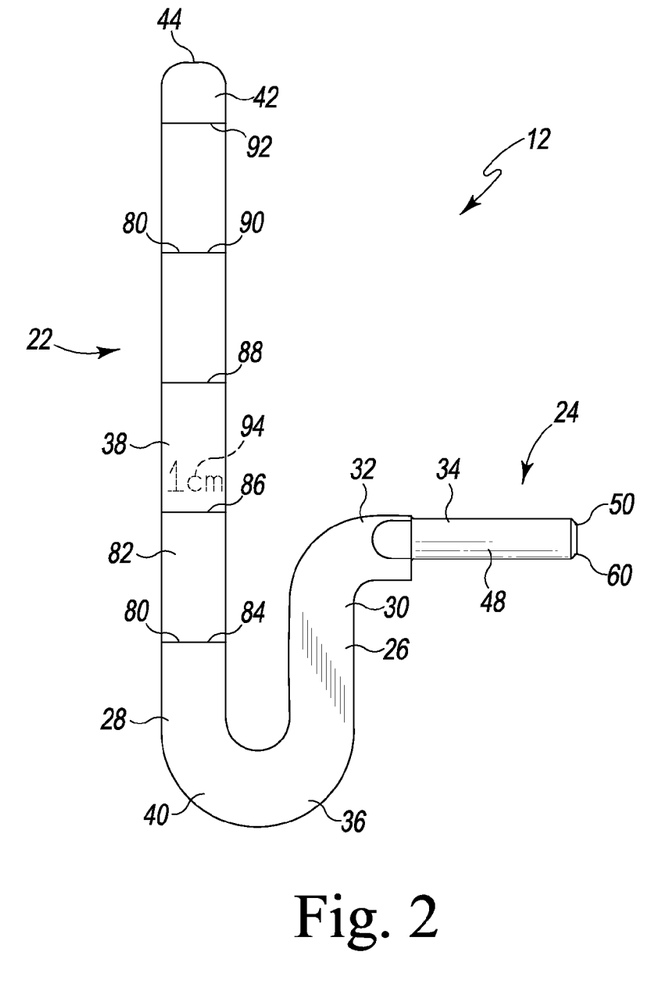
FIG. 2 is a side elevation view of a measurement gauge of the orthopaedic surgical instrument assembly of FIG. 1.
Figure 3:
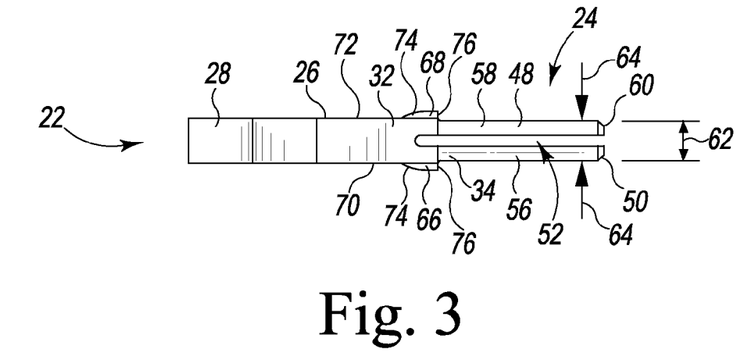
FIG. 3 is plan view of the measurement gauge of FIG. 2.

As shown in FIGS. 2 and 3, the measurement gauge 12 of the instrument assembly 10 includes an arm 22 and a mounting shaft 24 extending from the arm 22. The mounting shaft 24 is configured to engage the base cutting block 14 to secure the gauge 12 to the block 14. In the illustrative embodiment, the gauge 12 is formed as a single monolithic component from a metallic material such as, for example, a stainless steel or a cobalt chromium alloy. In other embodiments, the gauge 12 may be formed from two or more components that are later assembled. It should also be appreciated that in other embodiments the gauge 12 may be formed from a polymeric material such as, for example, a hard plastic. In still other embodiments, the gauge 12 and the base cutting block 14 may be formed as a single monolithic component.

In the illustrative embodiment, the arm 22 of the gauge 12 includes an inner segment 26 secured to the mounting shaft 24 and an outer segment 28 secured to the inner segment 26. The segments 26, 28 cooperate to define a J curve, as shown in FIG. 2. The inner arm segment 26 has a body 30 that extends from an upper end 32 secured to an end 34 of the mounting shaft 24 to a lower end 36. As shown in FIG. 2, the outer arm segment 28 has a lower end 40 secured to the lower end 36 of the inner arm segment 26. The outer arm segment 28 has a body 38 that extends from the lower end 40 to an upper end 42 of the segment 28. The upper end 42 of the outer segment 28 includes a tip 44 of the arm 22. When the gauge 12 is attached to the base cutting block 14, the tip 44 is positioned proximal to the base cutting block 14, as described in greater detail below.

The mounting shaft 24 of the gauge 12 has a cylindrical body 48 that extends from the end 34 to a tip 50. As shown in FIG. 3, the cylindrical body 48 has a slot 52 defined therein. The slot 52 extends from an opening 54 defined in the tip 50, through the end 34 of the shaft 24, and into the upper end 32 of the inner segment 26. The slot 52 divides the cylindrical body 48 into a pair of cantilevered rods 56, 58. The shaft tip 50 also includes a chamfer 60, and the cylindrical body 48 has an outer diameter 62. When force is applied in the direction indicated by arrows 64, the rods 56, 58 may be moved toward one another, thereby decreasing the outer diameter of the shaft 24.

In the illustrative embodiment, the gauge 12 also includes a pair of flanges 66, 68, which extend outwardly from the upper end 32 of the inner segment 26. As shown in FIG. 3, the flange 66 extends outwardly from an anterior surface 70 of the inner segment 26. The other flange 68 is positioned opposite the flange 66 on a posterior surface 72 of the inner segment 26. Each of the flanges 66, 68 has a curved face 74 and a flat face 78.

As shown in FIG. 2, the gauge 12 has a plurality of markings 80 defined thereon. As described in greater detail below, each marking 80 indicates a predetermined distance from a distal surface 104 of the base cutting block 14. The markings 80 are defined on an anterior surface 82 of the arm 22 between the lower end 40 and the upper end 42 of the outer segment 28. In the illustrative embodiment, each marking 80 is formed by etching the anterior surface 82. It should be appreciated that in other embodiments the markings 80 may be formed by, for example, stamping or printing. In the illustrative embodiment, the markings 80 include lines 84, 86, 88, 90, 92, each of which is spaced one centimeter apart. In other embodiments, the markings 80 may include additional lines, which may be spaced closer together. In still other embodiments, the markings 80 may include fewer lines, which may be spaced farther apart. The markings 80 may also include numerical indicators, such as, for example, indicator 94, which provide a numerical value of the distance between the lines 86, 88, 90, 92 and the reference line 84.

Figure 4:
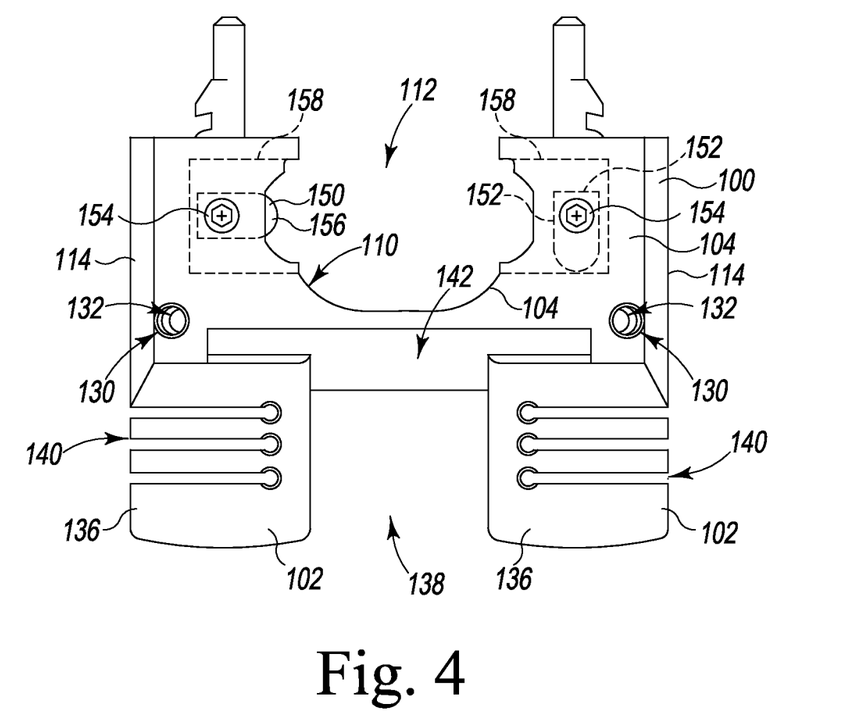
FIG. 4 is a plan view of a base cutting block of the orthopaedic surgical instrument assembly of FIG. 1.
Figure 5:
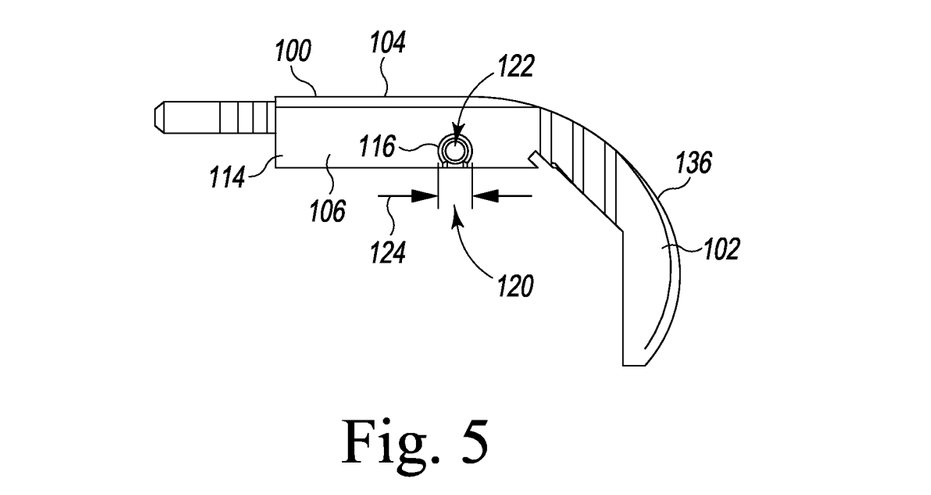
FIG. 5 is a side elevation view of the base cutting block of FIG. 4.
Figure 6:
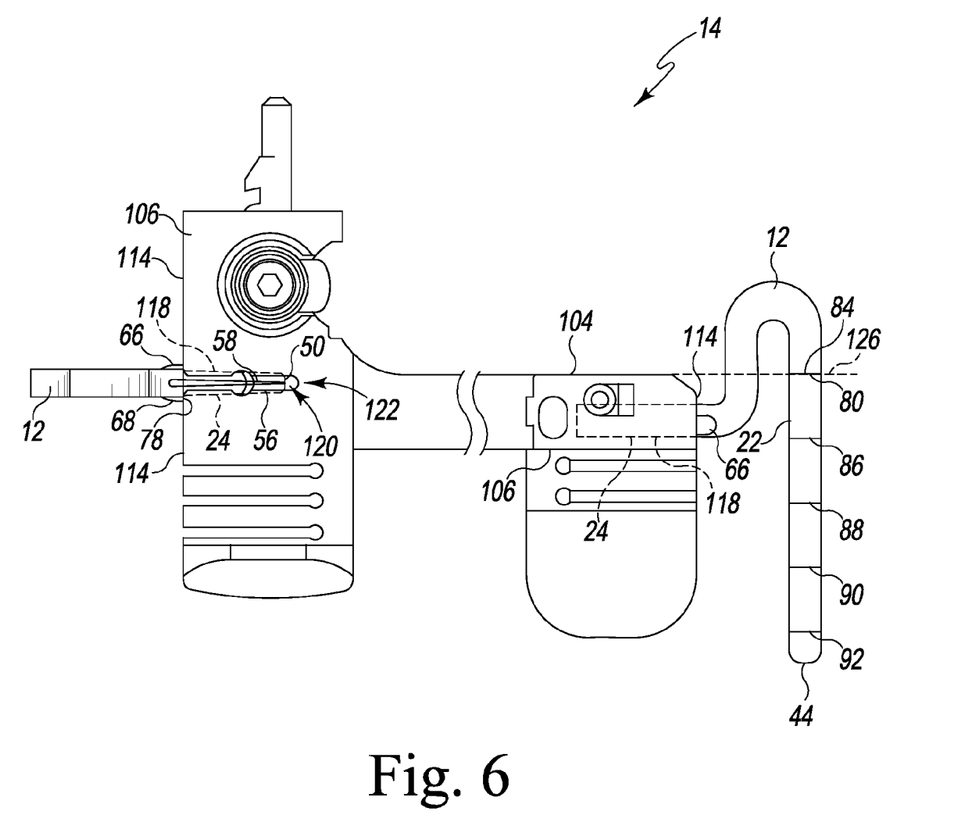
FIG. 6 is a fragmentary view of a pair of measurement gauges secured to the base cutting block.

Referring now to FIGS. 4-6, the base cutting block 14 includes a base plate 100 and a pair of arms 102 extending from the base plate 100. The base plate 100 and the arms 102 of the base cutting block 14 are formed from a metallic material, such as, for example, a stainless steel or a cobalt chromium alloy. The base plate 100 includes a distal surface 104 and a proximal surface 106 positioned opposite the distal surface 104. An opening 108 is defined in the distal surface 104, and an inner wall 110 extends distally through the base plate 100 to define a receiving slot 112. As described in greater detail below, the slot 112 is sized to permit the passage of the intramedullary adaptor 16 and the intramedullary surgical instrument 18.

The base plate 100 of the base cutting block 14 has a pair of side walls 114 that extend between the distal surface 104 and the proximal surface 106. Each side wall 114 has an opening 116 defined therein. As shown in FIG. 6, an inner wall 118 extends inwardly from each opening 116 to define a pair of channels 120 in the proximal surface 106 of the base plate 100. Each channel 120 includes a cylindrical bore 122 that is sized to receive the mounting shaft 24 of the gauge 12. As such, a gauge 12 may be secured to either side wall 114 of the base cutting block 14. In the illustrative embodiment, the cylindrical bore 122 has a diameter 124 that is less than the outer diameter 62 of the mounting shaft 24.

To secure a gauge 12 to the base cutting block 14, the tip 50 of the mounting shaft 24 is aligned with the opening 116 in the side wall 114 of the base plate 100. In the illustrative embodiment, the gauge 12 is oriented such that the tip 44 of the arm 22 is positioned proximal to the base cutting block 14, as shown in FIG. 6. The mounting shaft 24 may then be advanced into the opening 116. When the shaft tip 50 reaches the opening 116, the chamfer 60 of the shaft 24 engages the inner wall 118 of the block 14.

As described above, the outer diameter 62 of the shaft 24 is greater than the inner diameter 124 of the bore 122 of the block 14; as a result, the engagement between the chamfer 60 and the inner wall 118 presses rods 56, 58 of the shaft 24 toward one another. The outer diameter of the shaft 24 is thereby decreased such that the shaft 24 may be advanced into the bore 122. As shown in FIG. 6, when the mounting shaft 24 is fully seated in the bore 122, the flat faces 78 of the flanges 66, 68 engage the side wall 114 of the base cutting block 14. The rods 56, 58 of the mounting shaft 24 exert a radial force against the inner wall 118 of the block 14 to retain the mounting shaft 24 in the bore 122.

As such, the mounting shaft 24 acts as a self-retaining fastener that secures the measurement gauge 12 to the base cutting block 14. It should be appreciated that in other embodiments the instrument assembly 10 may include other fasteners such as, for example, screws, locks, retaining flanges, and so forth that secure the measurement gauge 12 to the base cutting block 14. As shown in FIG. 6, the base cutting block 14 has a pair of measurement gauges 12 secured thereto.

As shown in FIG. 6, the distal surface 104 of the base cutting block 14 defines an imaginary plane 126. When each gauge 12 is attached to the block 14, the line 84 of the markings 80 is positioned in the plane 126. In that way, the line 84 acts as a reference line for the other lines 86, 88, 90, 92 to indicate the distance of each of those lines from the distal surface 104 the block 14. In the illustrative embodiment, each of the lines 86, 88, 90, 92 is spaced approximately one centimeter apart. As such, the line 86 indicates a distance of one centimeter from the distal surface 104 of the base cutting block 14, the line 88 indicates a distance of two centimeters, the line 90 indicates a distance of three centimeters, and the line 92 indicates a distance of four centimeters. As described above, the gauge 12 may include additional or fewer lines in other embodiments.

Returning to FIG. 4, the base cutting block 14 also includes a pair of fastener guides 130 that are defined in the base plate 100. Each fastener guide 130 includes a bore 132 that is sized to receive fasteners such as, for example, fixation pins, which may be utilized to secure the base cutting block 14 to the patient's femur. It should be appreciated that in other embodiments the base cutting block 14 may include additional fastener guides 130 or other fastening elements to secure the cutting block to the patient's femur. Each channel 120 of the block 14 is aligned with one of the fastener guides 130 such that the bore 132 of the fastener guide 130 opens into the bore 122 of the channel 120.

As described above, the base cutting block 14 also includes a pair of arms 102 that extend posteriorly from a posterior side 134 of the base plate 100. Each arm 102 includes an articulating surface 136 shaped to match or correspond to a condylar surface of a femoral prosthetic component. In that way, the articulating surfaces 136 of the arms 102 are configured to contact a natural or prosthetic bearing surface of the patient's tibia. The arms 102 are spaced apart such that an opening 138 is defined therebetween.

The base cutting block 14 includes a number of cutting guides that may be used during an orthopaedic surgical procedure to resect a portion of a patient's femur. For example, as shown in FIG. 3, the base cutting block 14 includes a number of posterior cutting guides 140 defined in the arms 102 and a posterior chamfer cutting guide 142 defined in the base plate 100. Each cutting guide 140 includes an elongated slot sized to receive a cutting saw blade of a surgical saw or other surgical device.

As described above, the instrument assembly 10 also includes an intramedullary adaptor 16 that is configured to be coupled to the base cutting block 14 and a locking mechanism 20 that secures the intramedullary adaptor 16 to the base cutting block 14. In the illustrative embodiment, the locking mechanism 20 includes a pair of locking tabs 150, 152 pivotally coupled to the base cutting block 14. As shown in FIG. 4, each of the locking tabs 150, 152 is coupled to the block 14 via a joint 154, which permits each of the locking tabs 150, 152 to pivot between a locked position (see tab 150) and an unlocked position (see tab 152). In the locked position, an ear 156 of each of the locking tabs 150, 152 is positioned in the receiving slot 112 of the base cutting block 14 to thereby engage a surgical instrument (e.g., the intramedullary adaptor 16) positioned in the slot 112. In the unlocked position, each ear 156 is positioned in an aperture 158 and spaced apart from the receiving slot 112.

Returning to FIG. 1, the intramedullary adaptor 16 includes a mounting bracket 160 attached to a main body 162. The mounting bracket includes a pair of arms 164, 166 extending outwardly from the main body 162. A channel 168 is defined in the free end of each of the arms 164, 166. Each channel 168 is sized to receive one of the ears 156 of the locking tabs 150, 152. In the illustrative embodiment, the intramedullary adaptor 16 is formed from a metallic material, such as, for example, a stainless steel or a cobalt chromium alloy.

The adaptor 16 also includes a fastener 170 configured to secure the adaptor 16 to the intramedullary surgical instrument 18. The fastener 170 extends outwardly from the main body 162 of the adaptor 16 and includes a plurality of external threads 172. The fastener 170 is configured to rotate relative to the main body 162. In use, a surgeon may insert a driver or other surgical tool into an opening 174 defined in the adaptor 16 to rotate the fastener 170 relative to the main body 162.

As described above, the instrument assembly 10 includes an intramedullary surgical instrument 18 that may be secured to the adaptor 16. In the illustrative embodiment, the intramedullary surgical instrument 18 includes a stem stabilizer 180 and a stem trial 182. The stem stabilizer 180 and the stem trial 182 are formed from a metallic material, such as, for example, a stainless steel or a cobalt chromium alloy. It should be appreciated that in other embodiments the intramedullary surgical instrument may take other forms. For example, the stem stabilizer and/or the stem trial may be substituted for different sized instruments or different configurations. Additionally, in other embodiments, the intramedullary surgical instrument may take the form of a broach.

Figure 8:
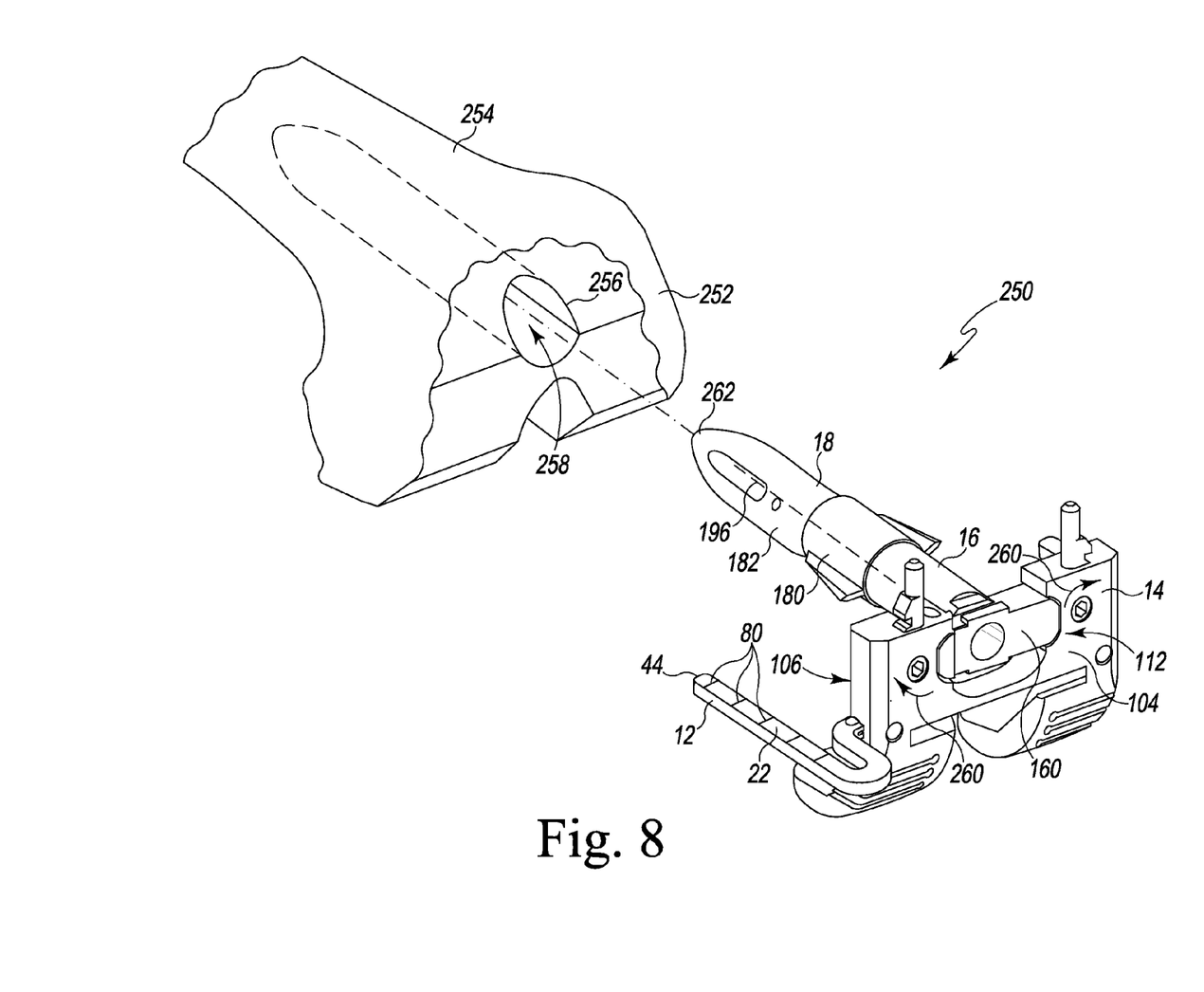
FIG. 8 is a perspective view of the orthopaedic instrument assembly of FIG. 1 positioned relative to a distal end of a patient's femur.

In the illustrative embodiment, the stem stabilizer 180 includes a cylindrical body 184 having a pair of fins 186 extending outwardly therefrom. It should be appreciated that in other embodiments the fins may be omitted. In still other embodiments, the stabilizer may include additional fins. The cylindrical body 184 has a central passageway 188 defined therein. As shown in FIG. 1, a cylindrical inner wall 190 defines the passageway 188 and has a plurality of internal threads 192 formed thereon that correspond to the external threads 172 formed on the fastener 170 of the adaptor 16. As such, the fastener 170 may be threaded into the passageway 188 to secure the stem stabilizer 180 to the adaptor 16. The internal threads 192 of the stem stabilizer 180 also correspond to the external threads 194 formed on the stem trial 182 such that the stem trial 182 may be threaded onto the stem stabilizer 180 to assemble the intramedullary surgical instrument 18. When the intramedullary surgical instrument 18 is assembled, the stem trial 182 and the stem stabilizer cooperate to define a longitudinal axis 196 of the intramedullary surgical instrument 18, as shown in FIG. 8.

The instrument assembly 10 may also include a plurality of modular cutting blocks configured to be coupled to the base cutting block 14. A number of modular cutting blocks suitable for use with the base cutting block 14 are shown and described in U.S. patent application Ser. No. 13/485,470 entitled "METHOD OF SURGICALLY PREPARING A PATIENT'S FEMUR," which issued as U.S. Pat. No. 9,050, 107 on Jun. 9, 2015 and is incorporated herein by reference. The instrument assembly 10 includes a locking or retention mechanism 200 that secures each modular cutting block to the base cutting block 14. In the illustrative embodiment, the retention mechanism 200 includes a pair of mounting brackets 202 attached to the base cutting block 14 and a corresponding pair of mounting brackets attached to each modular cutting block. The instrument assembly 10 also includes a cover 204 (see FIG. 10), which may be positioned over the mounting brackets 202 of the base cutting block 14 when none of the modular cutting blocks are secured to the base cutting block 14.

Figure 7:
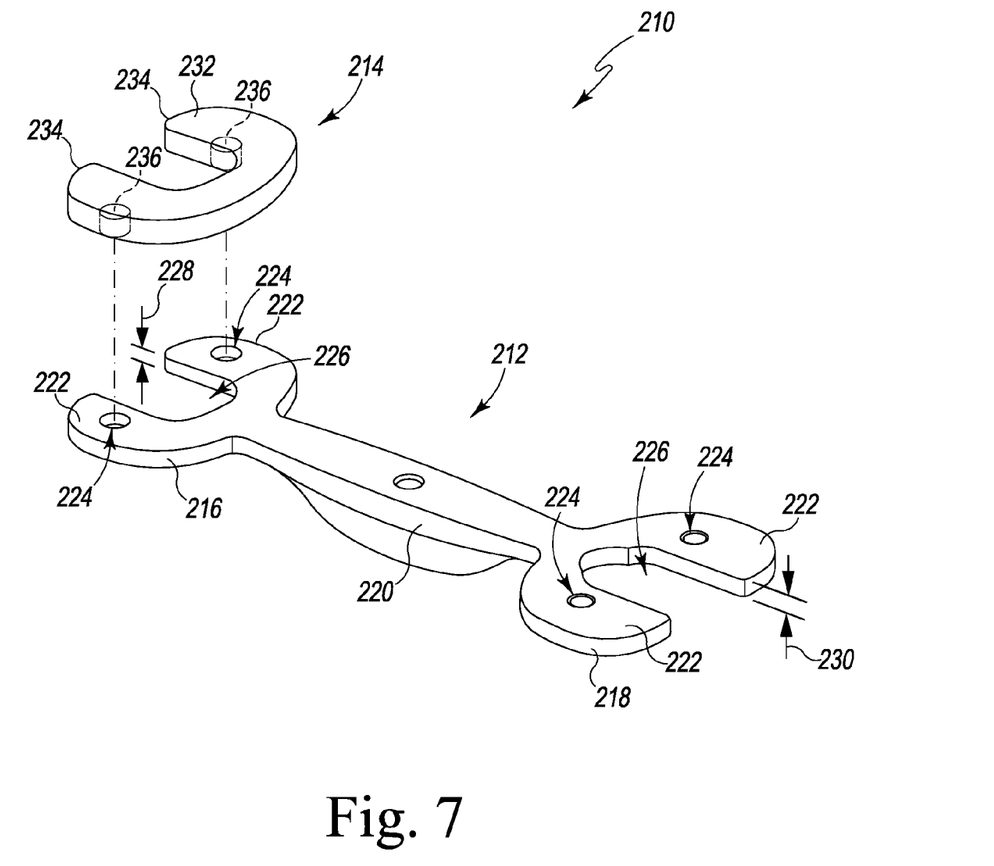
FIG. 7 is a perspective view of a gap assessment tool.

Referring now to FIG. 7, a gap assessment tool 210 is shown. The gap assessment tool 210 may be used in conjunction with the instrument assembly 10 to assess the joint space between a patient's femur and tibia including, for example, the flexion and extension gaps of the patient, and size the prosthetic implants. The gap assessment tool 210 includes a handle 212 and a plurality of shim blocks 214 configured to be secured to the handle 212. Only a single shim block 214 is shown in FIG. 7. The handle 212 has a spacer end 216, a spacer end 218 positioned opposite the spacer end 216, and a body 220 connecting the ends 216, 218. The handle 212 is formed from a metallic material, such as, for example, a stainless steel or a cobalt chromium alloy. It should also be appreciated that the handle 212 may be formed from a hard polymeric material.

Each of the spacer ends 216, 218 of the handle 212 includes a pair of arms 222 extending outwardly from the body 220. Each arm 222 has a bore 224 defined therein, and an opening 226 is defined between the arms 222. The spacer end 216 has a thickness 228 that corresponds to the thickness of a tibial trial. The spacer end 218 has a thickness 230 that corresponds to the thickness of another tibial trial. In the illustrative embodiment, the thicknesses 228, 230 of the spacer ends 216, 218 are different.

Each shim block 214 includes an articulation surface 232 configured to engage the distal surface 104 and the articulating surfaces 136 of the base cutting block 14. The shim blocks 214 are formed from a hard polymeric material, such as, for example, acetal. It should be appreciated that in other embodiments the blocks 214 may be formed from a metallic material, such as, for example, stainless steel or cobalt chromium. The shim block 214 has a pair of arms 234 that correspond to the arms 222 of the handle 212. Each arm 234 has a post 236 extending downwardly from a bottom surface 238. Each post 236 is sized to be received in each bore 224 defined in the handle 212. The shim block 214 may include a spring or other retention device to secure the shim block 214 to the handle 212.

As described above, the gap assessment tool 210 includes a plurality of shim blocks 214, each of which may be separately attached to the handle 212. Each shim block 214 has a different thickness such that the surgeon is able to assemble a gap assessment tool of one size and configuration, evaluate the performance, and then modify the gap assessment tool as necessary to determine intraoperatively the flexion and extension gaps of the patient, as described in greater detail below. Depending on the anatomy of a patient, the arms 222 of either of the spacer ends 216, 218 may engage the distal surface 104 and the articulating surfaces 136 of the base cutting block 14 without a shim block 214.

The assembly 10 and the assessment tool 210 may be utilized during the performance of an orthopaedic surgical procedure to implant a femoral prosthetic component in a patient. As shown in FIG. 8, an orthopaedic instrument construct 250 is formed from the intramedullary orthopaedic surgical instrument 18, the intramedullary adaptor 16, the base cutting block 14, and one or both measurement gauges 12. The orthopaedic instrument construct 250 is attached to a distal end 252 of a patient's femur 254, with the intramedullary orthopaedic surgical instrument 18 and the proximal end of the intramedullary adaptor 16 extending through a distal opening 256 of the patient's femur 254 and positioned in the medullary canal 258. The surgeon may perform a gap assessment and set femoral rotation. The surgeon may also use the construct 250 to begin resecting and shaping the distal end 252 of the patient's femur 254 to receive the femoral prosthetic component.

Prior to inserting the intramedullary orthopaedic surgical instrument 18 into the patient's medullary canal 258, an orthopaedic surgeon may remove a prior prosthetic implant and drill and/or ream the medullary canal 258 to receive the intramedullary orthopaedic surgical instrument 18. Multiple drills or reamers may be used to increase the size of opening 256 of the medullary canal 258 of the patient's femur 254. When the reaming operation is complete, the medullary canal 258 is configured as shown in FIG. 8 and is ready to receive the instrument 18.

After preparing the medullary canal 258, the surgeon may assemble the instrument construct 250 and insert the intramedullary orthopaedic surgical instrument 18 into the canal 258. To do so, the surgeon may select the intramedullary orthopaedic surgical instrument 18 from a plurality of intramedullary orthopaedic surgical instrument 18. For example, the surgeon may select a stem trial 182 and a stem stabilizer 180 from a plurality of stem trials and a plurality of stem stabilizers. The stem trials may vary in length, diameter, or other aspect, and the surgeon may select the stem trial 182 based on the patient's anatomy and the type of prosthetic stem component to be included in the femoral prosthesis. Similarly, the stem stabilizer may be selected based on the patient's anatomy and whether additional stability may be needed in the medullary canal 258. When the surgeon has selected an appropriate stem trial 182 and stem stabilizer 180, the surgeon may thread the stem trial 182 onto the stem stabilizer 180 to form the intramedullary orthopaedic surgical instrument 18 shown in FIG. 8.

It should also be appreciated that in other embodiments the stem trials and stem stabilizers may be formed as single, monolithic units of different sizes and configurations. It should also be appreciated that in other embodiments the intramedullary orthopaedic surgical instrument may take the form of a femoral broach having a plurality of teeth configured to engage the patient's femur 254 when inserted into the medullary canal 258.

After selecting the intramedullary orthopaedic surgical instrument, the surgeon may assemble the instrument construct 250. To do so, the surgeon may align the central passageway 188 of the stem stabilizer 180 with the fastener 170 of the intramedullary adaptor 16. The fastener 170 may be advanced into engagement with the threaded inner wall 190 of the stem stabilizer 180. A surgeon may use a driver or other surgical tool to rotate the fastener 170 to thread the fastener 170 into the stem stabilizer 180, thereby securing the intramedullary adaptor 16 to the intramedullary orthopaedic surgical instrument 18.

The intramedullary adaptor 16 may be then attached to the base cutting block 14. To do so, the mounting bracket 160 of the adaptor 16 is positioned in the receiving slot 112 of the base cutting block 14. A surgeon may use a driver or other surgical tool to rotate the locking tabs 150, 152 as indicated by arrows 260 in FIG. 8. As the locking tabs 150, 152 are rotated, the ears 156 are advanced into the corresponding channels 168 defined in the mounting bracket 160, thereby securing the adaptor 16 to the block 14. The surgeon may choose to attach the adaptor 16 to the base cutting block 14 before attaching the intramedullary orthopaedic surgical instrument 18 to the adaptor 16.

The gauge 12 may be secured to the base cutting block 14 as described above. The tip 50 of the mounting shaft 24 of the gauge is aligned with the opening 116 in the side wall 114 of the base plate 100. As shown in FIG. 8, the gauge 12 is oriented such that the tip 44 of the arm 22 is positioned proximal to the base cutting block 14. The mounting shaft 24 may then be advanced into the opening 116. As described above, when the shaft 24 is positioned in the bore 122, the rods 56, 58 of the mounting shaft 24 exert a radial force against the inner wall 118 of the block 14 to retain the mounting shaft 24 in the bore 122. As shown in FIG. 8, the outer segment 28 of the gauge 12 extends parallel to the longitudinal axis 196 of the intramedullary surgical instrument 18 when the gauge 12 is secured to the block 14.

After the instrument construct 250 is assembled, the surgeon may insert the intramedullary orthopaedic surgical instrument 18 into the medullary canal 258. To do so, the surgeon aligns the end 262 of the intramedullary orthopaedic surgical instrument 18 with the opening 256 of the canal 258 as shown in FIG. 8. The surgeon may advance the instrument construct 250 such that the intramedullary orthopaedic surgical instrument 18 is advanced through the opening 256 and into the canal 258. The fins 186 of the stem stabilizer 180 are moved into engagement with the femur 254. A mallet or other surgical tool may be used to drive the intramedullary orthopaedic surgical instrument 18 deeper into the medullary canal 258 to the position shown in FIG. 9.

Figure 9:
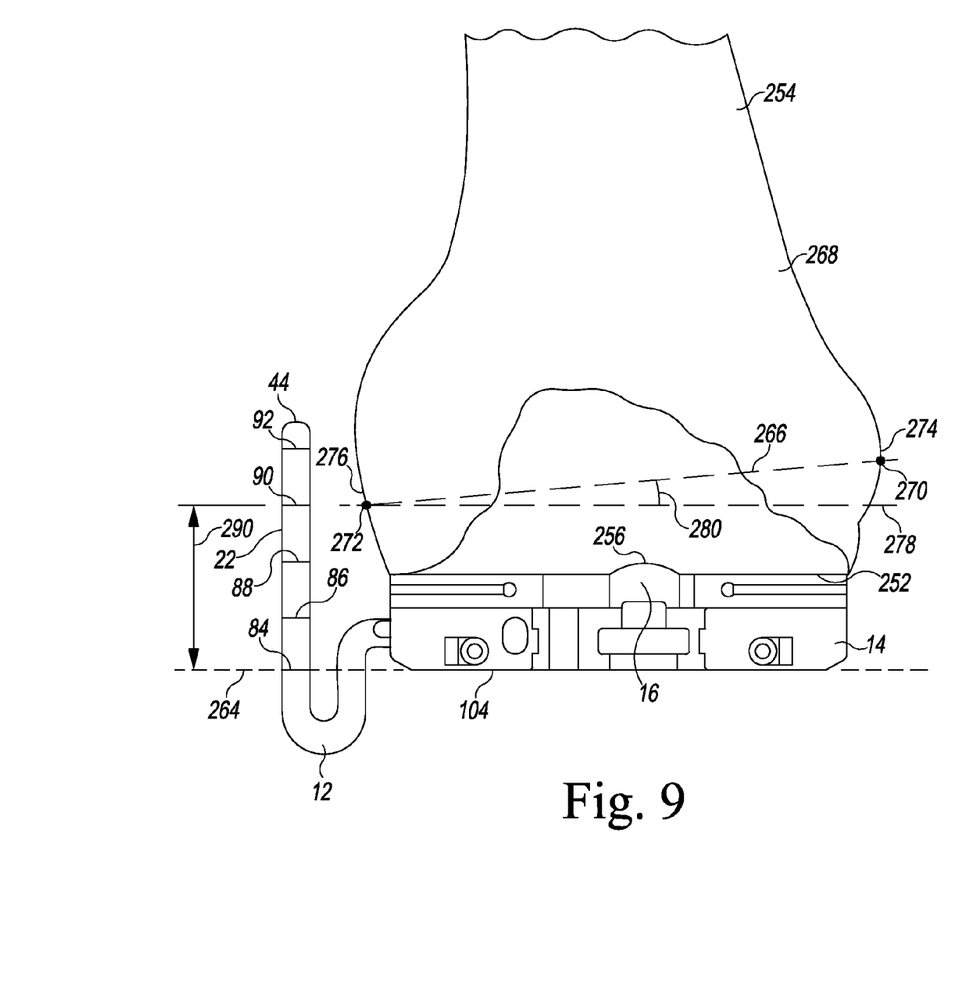
FIG. 9 is an anterior elevation view of the orthopaedic instrument assembly inserted into an intramedullary canal of the patient's femur.

In the illustrative embodiment, the distal surface 104 of the base cutting block 14 defines the level of the joint line 264. What is meant herein by "joint line" is the planned contact line between the prosthetic femoral component and the prosthetic tibial bearing of the knee prosthesis. The joint line 264 lies distal of the epicondylar axis 266 of the femur 254. As shown in FIG. 9, the epicondylar axis 266 extends across the anterior face 268 of the femur 254 between a medial end 270 and a lateral end 272. The medial end 270 lies on the medial epicondyle 274 and the lateral end 272 lies on lateral epicondyle 276 of the femur 254. A transverse plane 278 extends through the femur 254, and an angle 280 is defined between the epicondylar axis 266 and the transverse plane 278. In the illustrative embodiment, the angle 280 is approximately 5 degrees. In a typical knee joint, the joint line 264 lies approximately three centimeters distal of the medial epicondyle 274 and approximately 2.5 centimeters distal of the lateral epicondyle 276.

When each gauge 12 is attached to the block 14, the line 84 of the markings 80 of the gauge is coincident with the joint line 264, as shown in FIG. 9. The line 84 defined on the gauge 12 acts as a reference line for the other lines 86, 88, 90, 92 of the gauge 12 to indicate the distance of each of those lines from the distal surface 104 of the block 14 and hence from the joint line 264. Each of the lines 86, 88, 90, 92 of the gauge 12 may therefore provide an indication of the distance between the distal surface 104 of the block 14 and the epicondylar axis 266 and hence the distance between the joint line 264 and the epicondylar axis 266.

As such, the gauge 12 may be used to assess the position of the joint line 264 defined by the instrument construct 250. As shown in FIG. 9, the gauge 12 is positioned on the lateral side of the femur 254. The lateral end 272 of the epicondylar axis 266 is aligned with the line 90 of the gauge 12, indicating that a distance 290 is defined between the distal surface 104 of the block 14 (and hence the joint line 264) and the lateral epicondyle 276 of the femur 254. In the illustrative embodiment, the distance 290 is equal to approximately three centimeters. After using the gauge 12 to assess the position of the joint line 264, the surgeon may choose to drive the intramedullary surgical instrument 18 deeper into the femur 254, thereby decreasing distance between the joint line 264 and the epicondylar axis 266. Alternatively, the surgeon may choose to proceed with a gap assessment and set femoral rotation with the construct 250 positioned as shown FIG. 9.

If the surgeon proceeds with the assessing the gap, the surgeon may insert a driver or other surgical tool into the intramedullary adaptor 16 to engage the fastener 170 and loosen the connection between the adaptor 16 and the intramedullary orthopaedic surgical instrument 18. In that way, the adaptor 16 and the base cutting block 14 may be permitted to rotate relative to the intramedullary orthopaedic surgical instrument 18. The surgeon may also attach the cover 204 to the base cutting block 14 to cover the mounting bracket 202.

Figure 10:
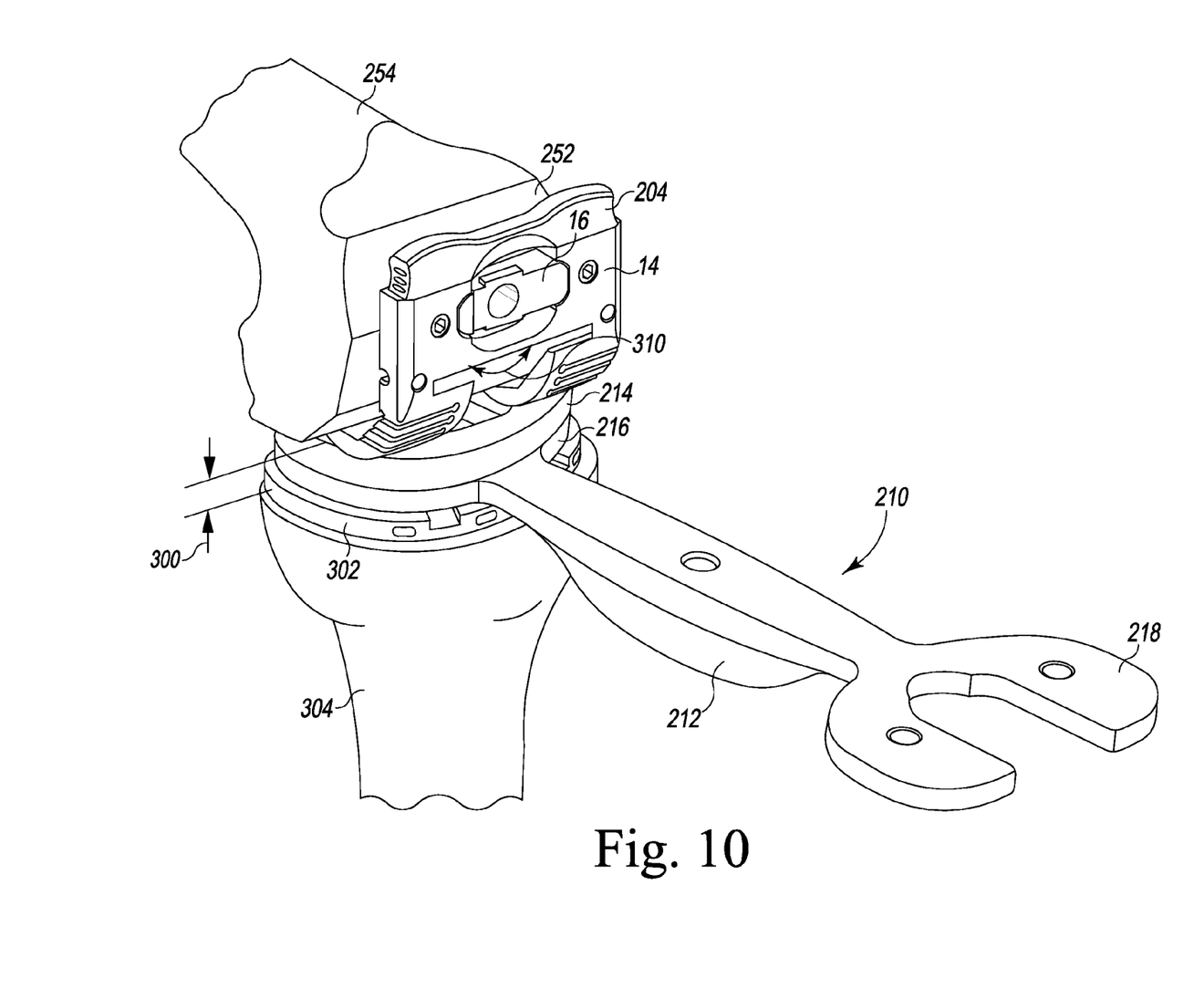
FIG. 10 is a perspective view of the orthopaedic instrument assembly of FIG. 1 and the gap assessment tool of FIG. 7 with the patient's leg in flexion.
Figure 11:
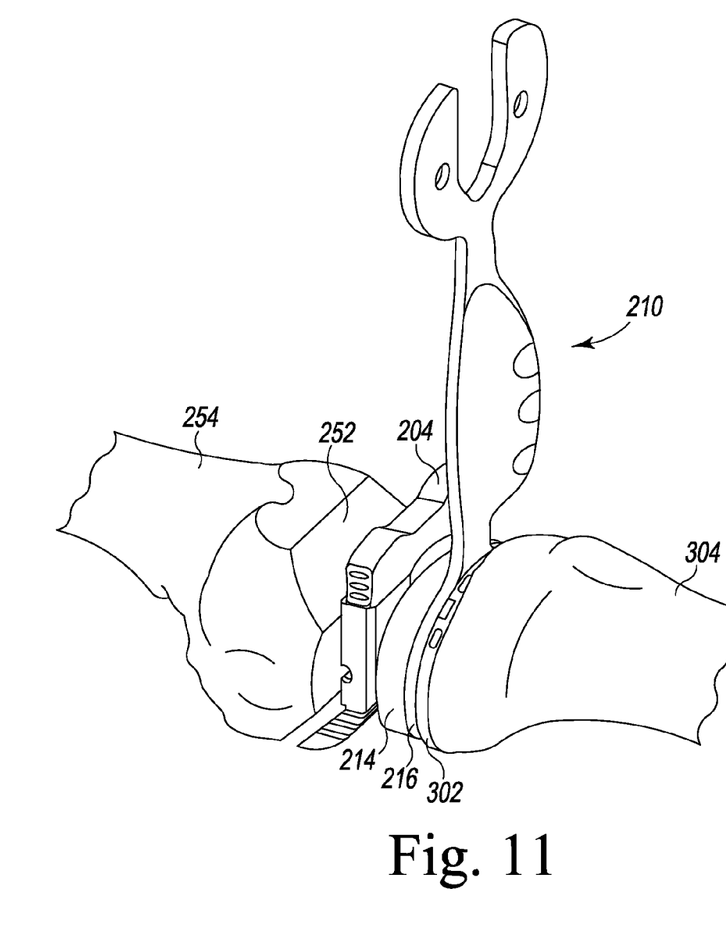
FIG. 11 is a view similar to FIG. 10 with the patient's leg in extension.

The surgeon may assess the flexion and extension gaps through the range of motion. To do so, the surgeon may remove the gauge 12, as shown in FIGS. 10 and 11, or keep the gauge 12 secured to the block 14. The surgeon may also assemble a gap assessment tool 210 to perform the assessment. The surgeon may use only the handle 212 and one of the spacer ends 216, 218 having a desired thickness. Alternatively, the surgeon may select a shim block 214. As shown in FIG. 10, the surgeon may attach the shim block 214 to one of the spacer ends 216, 218 of the handle 212 to obtain an appropriately sized gap assessment tool 210.

As shown in FIG. 10, a gap 300 is defined between the base cutting block 14 and a tibial trial component 302 attached to a patient's tibia 304. With the patient's knee in flexion as shown in FIG. 10, the surgeon may insert the gap assessment tool 210 into the gap 300. The surgeon may move the knee between flexion (FIG. 10) and extension (FIG. 11) to evaluate the gap 300 and the stability of the construct throughout the range of motion. The surgeon may substitute one shim block 214 for a shim block of different thickness to achieve the desired gap geometry. It should be appreciated that in other embodiments the gap assessment may be performed with another type of tensioning device, such as, for example, a laminar spreader.

The surgeon may also consider the femoral rotation of the base cutting block 14. To do so, the surgeon may balance the base cutting block 14 parallel to the tibial trial component 302 at 90 degrees of flexion as shown in FIG. 10. The surgeon may grasp the side walls 114 of the base cutting block 14 to rotate the base cutting block 14 in the direction indicated by arrow 310 until the gap 300 defined between the base cutting block 14 and the tibial trial component 302 is rectangular. When the base cutting block 14 is balanced, the surgeon may a driver or other surgical tool to rotate the fastener 170 to secure the intramedullary adaptor 16 to the intramedullary orthopaedic surgical instrument 18, thereby preventing relative movement between the adaptor 16 and the base cutting block 14 and the instrument 18.

Figure 12:
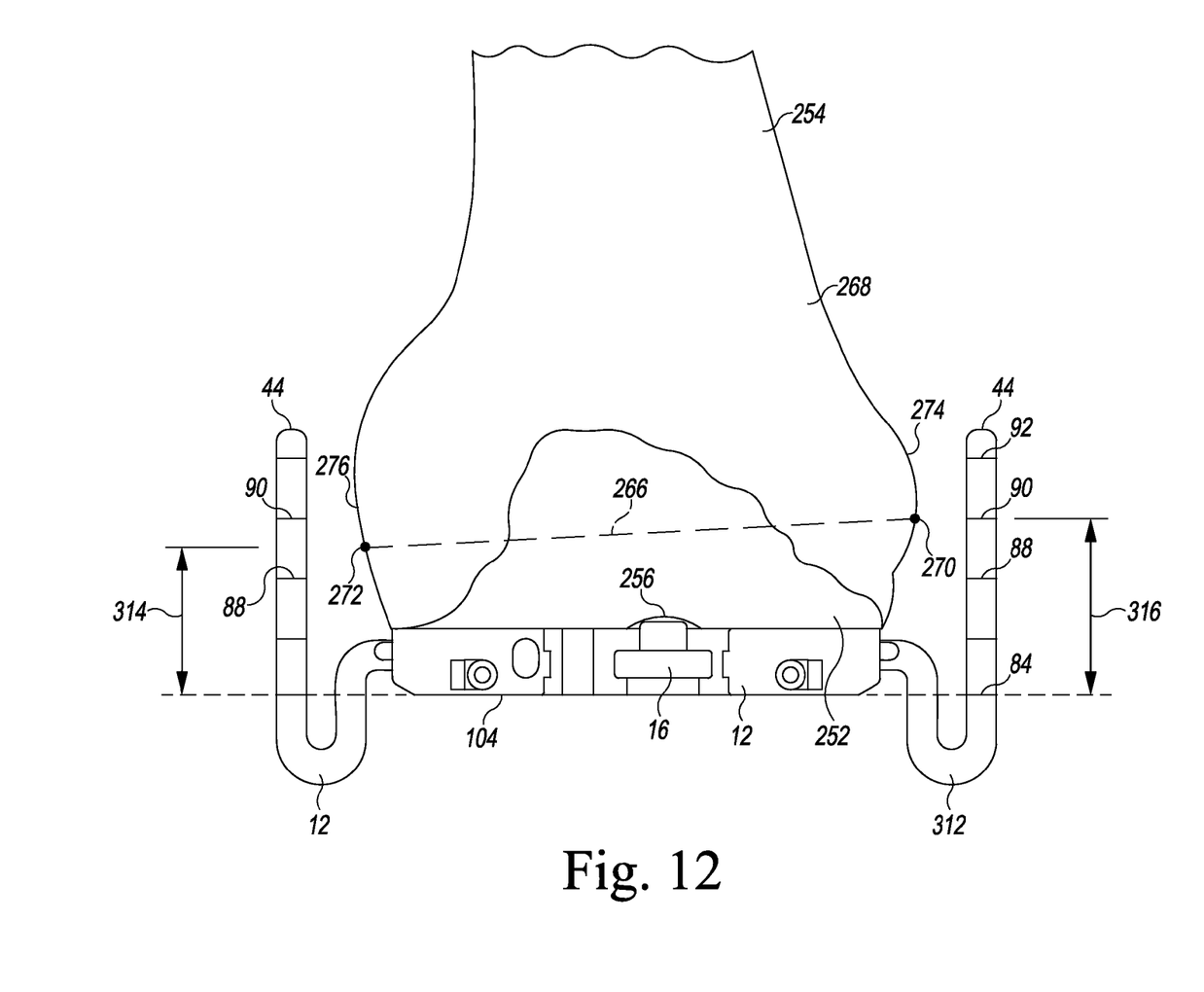
FIG. 12 is a view similar to FIG. 9 showing the base cutting block of the orthopaedic instrument assembly engaged with the distal end of the patient's femur.

After assessing the joint, the surgeon may choose to drive the intramedullary orthopaedic surgical instrument 18 deeper into the patient's femur 254, thereby changing the position of the joint line 264 and changing the size of the gap 300 when the leg is in extension. As described above, a mallet or other surgical tool may be used to drive the intramedullary orthopaedic surgical instrument 18 deeper into the medullary canal 258. The surgeon may drive the instrument construct 250 until the proximal surface 106 of the base cutting block 14 engages the distal end 252 of the patient's femur 254, as shown in FIG. 12. In that position, the lateral end 272 of the epicondylar axis 266 is positioned between the lines 88, 90 of the gauge 12, indicating that a distance 314 is defined between the distal surface 104 of the block 14 (and hence the joint line 264) and the lateral epicondyle 276 of the femur 254.

The surgeon may also attach another measurement gauge 312 to the base cutting block 14. As shown in FIG. 12, the medial end 270 of the epicondylar axis 266 is aligned with the line 90 of the gauge 312, indicating that a distance 316 is defined between the distal surface 104 of the block 14 (and hence the joint line 264) and the medial epicondyle 274 of the femur 254. After using the gauges 12, 312 to assess the position of the joint line 264, the surgeon may choose to reassess the gap 300 and reset the femoral rotation with the construct 250 positioned as shown FIG. 12.

If further adjustments are required, the surgeon may attach a distal cutting block similar to the distal cutting block shown and described in U.S. patent application Ser. No. 13/485,470 entitled "METHOD OF SURGICALLY PREPARING A PATIENT'S FEMUR," which issued as U.S. Pat. No. 9,050, 107 on Jun. 9, 2015 is incorporated herein by reference. The distal cutting block may be used to resect a portion of the patient's femur 254 to permit the surgeon to drive the intramedullary surgical instrument 18 deeper into the femur 254, thereby decreasing distance between the joint line 264 and the epicondylar axis 266.

When the instrument construct 250 is properly positioned relative to the distal end 252 of the patient's femur 254, the surgeon may proceed with further resections to shape the distal end 252 to receive the prosthetic femoral component. To do so, the surgeon may attach one or more modular cutting blocks to the base cutting block 14. The surgeon may also use the cutting guides 140, 142 to guide posterior and chamfer cuts of the distal end 252 of the patient's femur 254.

It should be appreciated that in other embodiments the measurement gauges 12, 312 may be secured to other orthopaedic surgical instruments that reference or attach to the distal surface of the femur. Other orthopaedic surgical instruments may include standalone distal cutting guide blocks or notch cutting guide blocks. Additionally, the gauges may be used with an insertion handle or other instrument configured to position a cutting block or other device on the distal surface of the femur. The gauges may also be attached to, for example, a femoral trial component, such as the femoral trial component shown and described in U.S. patent application Ser. No. 13/530,239 entitled "POLYMER FEMORAL TRIAL COMPONENT," which is expressly incorporated herein by reference.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument assembly comprising:
    a cutting guide block including a base plate having a distal surface, and a pair of curved arms extending posteriorly from the base plate, each curved arm including a posterior surface corresponding to a posterior condyle surface of a femoral prosthetic component, and
    a measurement gauge removably coupled to the cutting guide block, the gauge including (i) an arm having a tip positioned proximal to the base plate, and (ii) a plurality of markings defined on the arm, each marking indicating a predetermined distance between the marking and the distal surface of the base plate,
    wherein the base plate of the cutting guide block includes a bore defined in a medial surface thereof, and the gauge includes a shaft attached to the arm, the shaft being positioned in the bore of the base plate,
    wherein the arm of the gauge includes (i) a first segment having a first end secured to the shaft and a second end positioned distal to the base plate, and (ii) a second segment having a first end attached to the second end of the first segment and a second end including the tip of the arm, the first segment and the second segment defining a J curve, and
    wherein the markings of the gauge are defined on the second segment of the arm between the first end of the second segment and the second end of the second segment.

2. The orthopaedic surgical instrument assembly of claim 1, wherein the shaft of the gauge includes a spring pin configured to couple the gauge to the cutting guide block.

3. The orthopaedic surgical instrument assembly of claim 1, further comprising a second measurement gauge removably coupled to the cutting guide block, the second measurement gauge including (i) an arm having a tip positioned proximal to the base plate, and (ii) a plurality of second markings defined on the arm of the second measurement gauge, each second marking indicating a predetermined distance between the second marking and the distal surface of the base plate.

4. The orthopaedic surgical instrument assembly of claim 1, further comprising:
    an intramedullary orthopaedic surgical instrument configured to be inserted into a medullary canal of a patient's femur, and
    an adaptor removably coupled to the cutting guide block and the intramedullary orthopaedic surgical instrument.

5. An orthopaedic surgical instrument assembly comprising:
    an orthopaedic surgical instrument including a base plate having a distal surface and including a bore defined in a medial surface thereof,
    an intramedullary orthopaedic surgical instrument removably coupled to the orthopaedic surgical instrument, the intramedullary orthopaedic surgical instrument having an end positioned proximal to the orthopaedic surgical instrument that is configured to be inserted into a medullary canal of a patient's femur, and
    a measurement gauge removably coupled to the orthopaedic surgical instrument, the gauge including (i) an arm having a tip positioned proximal to the orthopaedic surgical instrument, (ii) a plurality of markings defined on the arm, each marking indicating a predetermined distance from the first surface of the orthopaedic surgical instrument, and (iii) a shaft attached to the arm, the shaft being positioned in the bore of the base plate,
    wherein the arm of the gauge includes (i) a first section extending from a first end secured to the shaft to a second end positioned distally of the distal surface of the base plate, and (ii) a second section extending from a first end attached to the second end of the first segment to a second end including the tip of the arm, and
    wherein the markings of the gauge are defined on the second section of the arm between the first end of the second section and the second end of the second section.

6. The orthopaedic surgical instrument assembly of claim 5, wherein the orthopaedic surgical instrument includes:
    a pair of curved arms extending posteriorly from the base plate.

7. The orthopaedic surgical instrument assembly of claim 5, wherein the intramedullary orthopaedic surgical instrument has a longitudinal axis, and the arm of the gauge includes a segment extending parallel to the longitudinal axis.

* * * * *